United States Patent
Adkins, Jr.

(10) Patent No.: US 11,260,094 B2
(45) Date of Patent: Mar. 1, 2022

(54) COMPOSITIONS, KITS AND METHODS FOR AMELIORATING OCULOPLASTIC POST-PROCEDURAL EFFECTS

(71) Applicant: OCuSOFT, Inc., Rosenberg, TX (US)

(72) Inventor: Nat Adkins, Jr., Rosenberg, TX (US)

(73) Assignee: OCuSOFT, Inc., Rosenberg, TX (US)

( * ) Notice: Subject to any disclaimer, the term of this patent is extended or adjusted under 35 U.S.C. 154(b) by 433 days.

(21) Appl. No.: 16/001,651

(22) Filed: Jun. 6, 2018

(65) Prior Publication Data

US 2018/0280460 A1    Oct. 4, 2018

Related U.S. Application Data

(60) Division of application No. 14/748,684, filed on Jun. 24, 2015, now Pat. No. 9,999,642, which is a continuation of application No. 14/059,262, filed on Oct. 21, 2013, now abandoned.

(51) Int. Cl.

| | |
|---|---|
| *A61K 36/28* | (2006.01) |
| *A61K 31/122* | (2006.01) |
| *A61K 31/704* | (2006.01) |
| *A61K 9/00* | (2006.01) |
| *A61K 31/085* | (2006.01) |
| *A61K 31/19* | (2006.01) |
| *A61K 31/23* | (2006.01) |
| *A61K 31/355* | (2006.01) |
| *A61K 31/4166* | (2006.01) |
| *A61K 31/593* | (2006.01) |
| *A61K 31/665* | (2006.01) |
| *A61K 47/02* | (2006.01) |
| *A61K 47/10* | (2017.01) |
| *A61K 47/12* | (2006.01) |
| *A61K 47/14* | (2017.01) |
| *A61K 47/24* | (2006.01) |
| *A61K 47/34* | (2017.01) |
| *A61K 47/36* | (2006.01) |
| *A61K 47/44* | (2017.01) |

(52) U.S. Cl.
CPC ............ *A61K 36/28* (2013.01); *A61K 9/0014* (2013.01); *A61K 31/085* (2013.01); *A61K 31/122* (2013.01); *A61K 31/19* (2013.01); *A61K 31/23* (2013.01); *A61K 31/355* (2013.01); *A61K 31/4166* (2013.01); *A61K 31/593* (2013.01); *A61K 31/665* (2013.01); *A61K 31/704* (2013.01); *A61K 47/02* (2013.01); *A61K 47/10* (2013.01); *A61K 47/12* (2013.01); *A61K 47/14* (2013.01); *A61K 47/24* (2013.01); *A61K 47/34* (2013.01); *A61K 47/36* (2013.01); *A61K 47/44* (2013.01)

(58) Field of Classification Search
None
See application file for complete search history.

(56) References Cited

U.S. PATENT DOCUMENTS

| | | |
|---|---|---|
| 4,101,652 A | 7/1978 | Bonati |
| 5,080,901 A | 1/1992 | Hangay et al. |
| 5,118,671 A | 6/1992 | Bombardelli et al. |
| 6,555,118 B1 | 4/2003 | Niazi et al. |
| 6,562,355 B1 | 5/2003 | Renault |
| 7,544,375 B1 | 6/2009 | Bellin et al. |
| 8,410,079 B2 | 4/2013 | Peter et al. |
| 2005/0080056 A1 | 4/2005 | Horn |
| 2006/0030697 A1 | 2/2006 | Singh |
| 2012/0121675 A1 | 5/2012 | Garcia-Sanz et al. |

OTHER PUBLICATIONS

Klapper et al., Management of Cosmetic Eyelid Surgery Complications, 2007, Semin Plat Surg, 21: 80-94.*
USPTO Office Action dated Feb. 25, 2015 for parent U.S. Appl. No. 14/059,262.
Nutrition Aid Center 2010 (http://web.archive.org/web/201 001 05054 135/http://totalnutritionaid.com/nature -pure-anti-rednessbotanical- serum-1-oz-serum-npl-42.html).

* cited by examiner

*Primary Examiner* — Terry A McKelvey
*Assistant Examiner* — Catheryne Chen
(74) *Attorney, Agent, or Firm* — D'Ambrosio & Menon, PLLC; Usha Menon

(57) ABSTRACT

Embodiments of the invention are directed to compositions, kits and methods for minimizing unsightly post-procedural effects associated with an oculoplastic procedure. The composition can include escin, *arnica* and phytonadione in a pharmacologically acceptable carrier.

9 Claims, No Drawings

COMPOSITIONS, KITS AND METHODS FOR AMELIORATING OCULOPLASTIC POST-PROCEDURAL EFFECTS

CROSS-REFERENCE TO RELATED APPLICATION(S)

This application is a divisional of and claims priority to U.S. Ser. No. 14/748,684 filed on Jun. 24, 2015, entitled "Compositions, Kits and Methods for Ameliorating Oculoplastic Post-Procedural Effects," which claims priority to U.S. application Ser. No. 14/059,262 filed Oct. 21, 2013, also entitled "Compositions, Kits and Methods for Ameliorating Oculoplastic Post-Procedural Effects," now abandoned, the contents of which are incorporated herein by reference in its entirety.

FIELD OF THE INVENTION

Compositions for topical application to the skin which comprise escin, *arnica* and phytonadione.

SUMMARY

According to one embodiment, a composition, formulated to minimize one or more post-procedural effects associated with an oculoplastic procedure, includes escin, *arnica* and phytonadione.

According to another embodiment, a method of minimizing one or more post-procedural effects associated with an oculoplastic procedure includes applying a therapeutically effective of a composition at or around the site of the oculoplastic procedure. The topical composition includes escin, *arnica* and phytonadione.

According to yet another embodiment, a post-oculoplastic procedure recovery kit includes a composition consisting essentially of escin; *arnica*; phytonadione; glycerin stearate; glyceryl stearate citrate; glycerin; stearic acid; sunflower oil; phenoxyethanol; dimethicone; tocopheryl acetate; allantoin; retinyl palmitate; cholecalciferol; sodium ascorbyl phosphate; cetearyl alcohol; lecithin; potassium sorbate; caprylic triglyceride; xanthan gum; sodium bicarbonate; and deionized water.

These and other aspects of the present invention will be better understood by reference to the following detailed description.

DETAILED DESCRIPTION

All terms used herein are intended to have their ordinary meaning unless otherwise provided.

Oculoplastics, or oculoplastic surgery, includes a variety of procedures, including surgical procedures, that deal with the orbit (eye socket), eyelids, tear ducts, and the face. Oculoplastic procedures include blepharoplasty and other cosmetic surgeries that involve, for example, cosmetic filler injections and botulinum toxin injections to temporarily improve the appearance of vertical frown lines. Blepharoplasty is sometimes performed in conjunction with facial resurfacing, in which lines around the eyes are removed with a laser or a chemical peel. Oculoplastic procedures can result in unsightly post-procedural effects. For example, many patients or subjects experience some degree of bruising or swelling at and/or around the treated area or site. During cosmetic procedures, when the injection needle is inserted into the facial muscles, it may puncture a blood vessel. This may cause blood to hemorrhage from the capillaries. The intradermal cutaneous hemorrhage can show up as a bruise. Physicians or clinicians typically apply pressure on the injected site to stop any bleeding and prevent bruising. However, if the bleeding cannot be completely stopped, the patient may experience bruising. In some instances, patients may experience delayed bruising. This is due to the fact that, in these patients, it may be a while before the blood inside their skin migrates to the surface of the skin. As used herein, the term "bruise" includes red or bluish-black marks, or any discoloration of the skin due to the release of blood from the capillaries into the tissues under the skin as a result of the oculoplastic procedure.

Although the physician's skill may play a role in minimizing these side-effects, it is almost impossible to eliminate some bruising and other side-effects of an oculoplastic procedure. These side-effects can last from a few hours to a few days. Post-procedure, the patient can apply makeup to conceal any minor bruising and ice to reduce any swelling. In some case, the patient may be advised to take oxidant rich foods and supplements until the patient is free of bruising. In some cases, the supplements may not be regulated by the Food and Drug Administration (FDA). Some patients may experience adverse side-effects (due to reactions with other medications) from ingesting some of these non-FDA regulated supplements. Therefore, there is a need for a non-ingestible composition that helps reduce or eliminate bruising, scarring, swelling and other similar effects caused by an oculoplastic procedure. Such a composition should be able to minimize skin discoloration and reduce bruising. Such a composition must also be non-toxic.

Embodiments of the present invention include non-toxic compositions, kits and methods for treating or minimizing one or more post-procedural effects associated with an oculoplastic procedure. The composition can be administered to a patient in a pharmacologically acceptable form selected from creams, ointments, gels, lotions, solutions and emulsions. A therapeutically effective amount of the composition can be administered to a patient prior to or soon after an oculoplastic procedure. For the purposes of this application, the term "therapeutically effective" indicates that a pre-determined amount of the composition is applied to the skin, wherein the amount is sufficient to reduce the time required to heal a post-oculoplastic procedure bruise, scar or swelling. The required dosage and duration of administration can be adjusted based on, for example, the age of the patient, visible improvements in the appearance of the bruise and other physiological indicators.

Administration of the composition can result in a visible improvement in one or more unsightly post-procedural effect, including, bruising, skin discolorations and swelling. The composition can be administered topically or locally to the skin at and/or around the site/area of the oculoplastic procedure. As used herein, the term "administration" means applying a therapeutically effective amount of the composition to the skin such that any unsightly post-procedural effects, such as, bruising, skin discolorations and swelling are treated to speed up their resolution.

In an embodiment, the composition can include escin, *arnica* and phytonadione in a pharmaceutically acceptable carrier. In one embodiment, the composition includes at least 2% escin or aescin. Escin improves circulation and eases post-procedural swelling. Escin is derived from horse chestnut (*Aesculus hippocastanum*). Arnica is extracted from the plant *Arnica Montana*. *Arnica* reduces inflammation and bruising. Phytonadione or Vitamin K is a fat-soluble vitamin that the body needs for blood coagulation. Vitamin K is associated with veins and blood because it is a factor in the blood's ability to clot. Vitamin K can minimize skin discolorations. Accordingly, in one embodiment, the composition including escin, *arnica* and phtyonadione reduces bruising and eases swelling by strengthening capillaries and improving circulation.

The composition further includes one or more vitamins or antioxidants to eliminate scars and reduce bruising. For example, in one embodiment, the composition can include one or more of tocopheryl acetate, cholecalciferol, rose hip seed oil, retinyl palmitate and sodium ascorbyl phosphate to minimize scarring and bruising when applied to the skin.

The composition includes shea butter and deionized water. The composition can further include a stabilizer and one or more emulsifiers such as an amphoteric, anionic, cationic or nonionic emulsifier, used alone or as a mixture, and optionally a co-emulsifier. The emulsifiers are chosen in an appropriate manner according to the emulsion to be obtained. The composition can include vegetable derived glycerine to reduce redness and increase moisture. The composition can include a vegetable derived glucoside-based emulsifier. In one embodiment, the composition can include cetostearyl alcohol, cetearyl alcohol or cetylstearyl alcohol, glyceryl monostearate or glyceryl stearate, glyceryl stearate citrate and stearic acid. The composition can further include xanthan gum for ensuring flowability of the composition.

The composition further includes one or more emollients. In one embodiment, the composition includes aloe barbanesis leaf juice or aloe vera. Aloe is known to have healthful benefits and can ease swelling or inflammation and help speed up the healing recovery process. The composition can further include sunflower oil, dimethicone, lecithin and caprylic/capric triglyceride and/or combinations thereof.

The composition further includes one or more antibacterial agents such as potassium sorbate and phenoxyethanol and a sulfur compound such as methylsulfonylmethane. The composition may further include allantoin. Allantoin is anti-irritant and skin protectant that also promotes the healing of scars. The composition can further include a stabilizer such as xanthan gum and a buffer such as sodium bicarbonate.

According to one embodiment, the composition consists essentially of escin, *arnica*, phytonadione, glycerin stearate, glyceryl stearate citrate, glycerin, stearic acid, sunflower oil, phenoxyethanol, dimethicone, tocopheryl acetate, allantoin, retinyl palmitate, cholecalciferol, sodium ascorbyl phosphate, cetearyl alcohol, lecithin, potassium sorbate, caprylic triglyceride, xanthan gum, sodium bicarbonate, and deionized water. This specific list of ingredients, which includes a high number of active ingredients, specifically and comprehensively addresses the need for a topical composition that can minimize bruising or swelling after an oculoplastic procedure in a single cosmetic product. In one embodiment, the composition can be devoid of dextran sulfate mixtures and/or a steroid.

According to another embodiment, a patient recommended for an oculoplastic procedure is identified as a candidate for receiving post procedure treatment. For instance, the patient may be known to be easily susceptible to bruising. Some patients may be susceptible to bruising due thinning and/or loss of elasticity of the skin due to illness or aging. Such patients can be administered a therapeutically effective amount of the composition in a pharmaceutically acceptable medium prior to and/or after the oculoplastic procedure. For example, a cream or lotion can be administered by gently rubbing onto the skin at or around the site of the oculoplastic procedure. The composition is allowed to penetrate the skin such that any unsightly post-procedural effects, such as, bruising, skin discolorations and swelling are treated, inhibited or reduced.

The composition is non-toxic and any residue can be safely left on the skin. The composition can be re-applied, as needed, periodically. For example, the composition used may be administered more than once daily. When topically applied, the composition ameliorates the undesired effects of an oculoplastic procedure. The composition can accelerate/reduce the time required to heal a bruise, swelling or scar caused by the oculoplastic procedure. Thus, the application of the composition can have a curative effect.

According to yet another embodiment, a post-oculoplastic procedure recovery kit includes a topical composition consisting essentially of escin, *arnica*, phytonadione, glycerin stearate, glyceryl stearate citrate, glycerin, stearic acid, sunflower oil, phenoxyethanol, dimethicone, tocopheryl acetate, allantoin, retinyl palmitate, cholecalciferol, sodium ascorbyl phosphate, cetearyl alcohol, lecithin, potassium sorbate, caprylic triglyceride, xanthan gum, sodium bicarbonate, and deionized water. The kit further includes housing for the composition. The kit can further include instructions for the application of the composition.

The embodiments of the invention provide methods, kits and compositions for cosmetic and therapeutic uses. It will also be appreciated that the composition can be employed in combination therapies, that is, administered concurrently with, prior to, or subsequent to, one or more other desired therapeutics or medical procedures taking into account the desired therapeutic effect to be achieved.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. For instance, the composition can also be used to treat any bruising caused by any (non-oculoplastic) procedure that causes blood to escape into surrounding tissue. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention. While composition, kits and methods are described in terms of "comprising," "containing," or "including" various components or steps, the compositions, kits and methods also can "consist essentially of" or "consist of" the various components and steps. In particular, every range of values (of the form, "from about a to about b," or, equivalently, "from approximately a to b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A method of minimizing one or more post-procedural effects associated with an oculoplastic procedure in a subject, comprising:

administering a therapeutically effective amount of a composition to the skin after the oculoplastic procedure; and allowing the composition to penetrate the skin such that a post-procedural effect is treated, inhibited and/or reduced, wherein the composition consists essentially of:
  Shea butter;
  aloe vera;
  Rosehip seed oil;
  escin;
  *arnica;*
  phytonadione;
  glycerin stearate;
  glyceryl stearate citrate;
  glycerin;
  stearic acid;
  sunflower oil;
  phenoxyethanol;
  dimethicone;
  tocopheryl acetate;
  allantoin;
  retinyl palmitate;
  cholecalciferol;
  sodium ascorbyl phosphate;
  cetearyl alcohol;
  potassium sorbate;
  caprylic triglyceride;
  xanthan gum;
  sodium bicarbonate; and
  deionized water.

2. The method according to claim 1, wherein the oculoplastic procedure comprises a facial procedure or surgery.

3. The method according to claim 2, wherein the administering the composition further comprises applying the composition to the skin surface.

4. The method according to claim 3, further comprising applying the composition at or around a site of the oculoplastic procedure.

5. The method according to claim 1, wherein the composition is administered in a pharmacologically acceptable form selected from a group consisting of creams, ointments, gels, lotions, solutions and emulsions.

6. The method according to claim 1, wherein the post-procedural effect is selected from the group consisting of a bruise, scar, skin discoloration and swelling.

7. The method according to claim 3, wherein the applied amount of the composition is sufficient to reduce a healing time of a post-procedural bruise and/or scar.

8. The method according to claim 1, further comprising identifying the subject for the oculoplastic procedure.

9. The method according to claim 1, further comprising providing the composition for administration.

* * * * *